United States Patent
Borsari

(10) Patent No.: US 11,565,073 B2
(45) Date of Patent: Jan. 31, 2023

(54) METHOD FOR CONTROLLING A THERMOREGULATED VENTILATION CIRCUIT

(71) Applicant: DIMAR S.r.l., Medolla (IT)

(72) Inventor: Maurizio Borsari, Mirandola (IT)

(73) Assignee: DIMAR S.r.l., Medolla (IT)

(*) Notice: Subject to any disclaimer, the term of this patent is extended or adjusted under 35 U.S.C. 154(b) by 924 days.

(21) Appl. No.: 16/419,530

(22) Filed: May 22, 2019

(65) Prior Publication Data

US 2019/0358423 A1 Nov. 28, 2019

(30) Foreign Application Priority Data

May 22, 2018 (IT) .................. 102018000005588

(51) Int. Cl.
*A61M 16/00* (2006.01)
*A61M 16/16* (2006.01)
(Continued)

(52) U.S. Cl.
CPC .......... *A61M 16/16* (2013.01); *A61M 16/022* (2017.08); *A61M 16/0875* (2013.01);
(Continued)

(58) Field of Classification Search
CPC .............. A61M 16/16; A61M 16/0883; A61M 16/1095; A61M 16/022; A61M 16/0875; A61M 2205/3368
See application file for complete search history.

(56) References Cited

U.S. PATENT DOCUMENTS 10,016,573 B2 * 7/2018 Shushunov ....... A61M 16/1075
2009/0107493 A1 * 4/2009 Liu ..................... A61M 16/16
392/394
(Continued)

FOREIGN PATENT DOCUMENTS

AU 2013204262 A1 3/2014
EP 1 352 670 A1 10/2003
(Continued)

OTHER PUBLICATIONS

Italian Search Report dated Jan. 18, 2019 in Italian application 201800005588, filed on May 22, 2018 (with English Translation of Categories of Cited Documents).

*Primary Examiner* — Steven O Douglas
(74) *Attorney, Agent, or Firm* — Oblon, McClelland, Maier & Neustadt, L.L.P.

(57) ABSTRACT

The present invention relates to a method for controlling a thermoregulated ventilation circuit (100) equipped with a control unit (40) and comprising an active humidifier (10). The active humidifier (10) further comprises, in turn, a cartridge (20) equipped with a humidification chamber (21) adapted to contain water to be heated for the humidification of the air through a heating element (30), and the thermoregulated circuit (100) further comprising at least one intake tube (120) for conveying the air exiting said cartridge and provided with heating means (123) for heating the air exiting said cartridge (20). The method according to the present invention is characterised in that said control unit (40) receives in input the patient's temperature data (Tp) detected by a patient's temperature probe (132) and regulates the operation of said heating element (30) of said cartridge (20) and the operation of said heating means (123) of the air exiting said cartridge (20) as a function of said patient's temperature (Tp).

10 Claims, 3 Drawing Sheets

(51) Int. Cl.
*A61M 16/08* (2006.01)
*A61M 16/10* (2006.01)

(52) U.S. Cl.
CPC .... *A61M 16/0883* (2014.02); *A61M 16/1095* (2014.02); *A61M 2205/3368* (2013.01)

(56) References Cited

U.S. PATENT DOCUMENTS

| | | | |
|---|---|---|---|
| 2009/0110029 A1* | 4/2009 | Bradley | A61M 16/024 |
| | | | 374/208 |
| 2011/0120462 A1 | 5/2011 | Tatkov et al. | |
| 2014/0166005 A1 | 6/2014 | Tatkov et al. | |
| 2015/0020803 A1* | 1/2015 | Dunlop | A61M 16/1095 |
| | | | 128/203.14 |
| 2015/0048530 A1 | 2/2015 | Cheung et al. | |
| 2016/0310689 A1 | 10/2016 | Osborne et al. | |
| 2018/0280651 A1 | 10/2018 | Liu et al. | |

FOREIGN PATENT DOCUMENTS

| | | |
|---|---|---|
| EP | 2 055 340 A1 | 5/2009 |
| WO | WO 2009/145646 A1 | 12/2009 |
| WO | WO 2013/147623 A1 | 10/2013 |
| WO | WO 2015/093989 A1 | 6/2015 |
| WO | WO 2017/043981 A1 | 3/2017 |
| WO | WO 2017/126980 A2 | 7/2017 |

\* cited by examiner

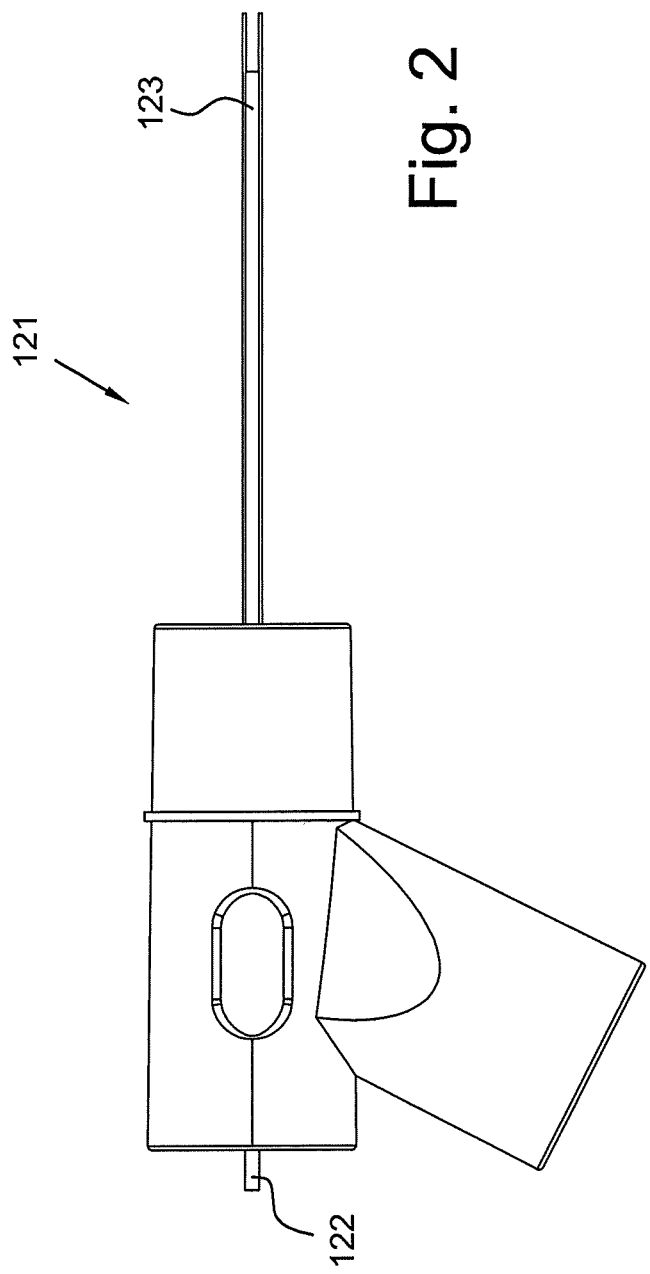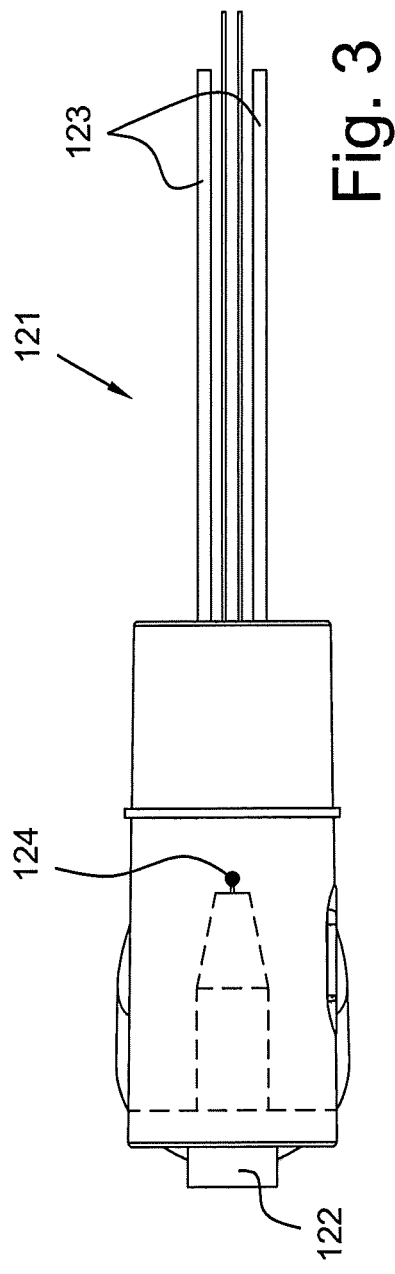

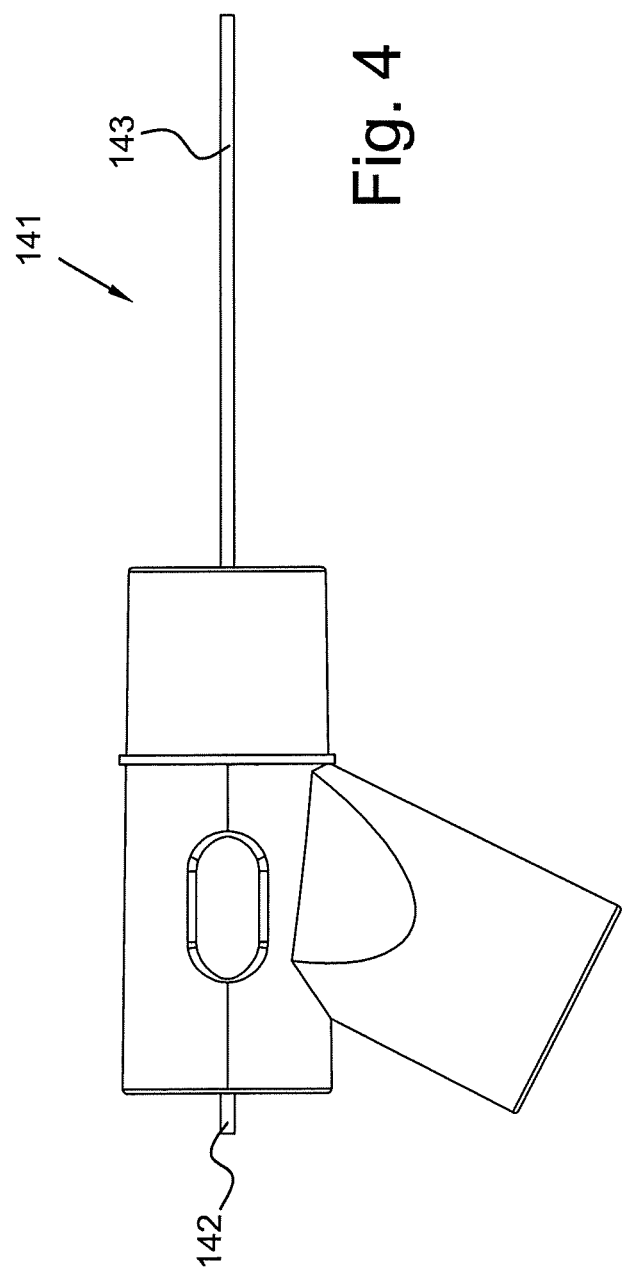
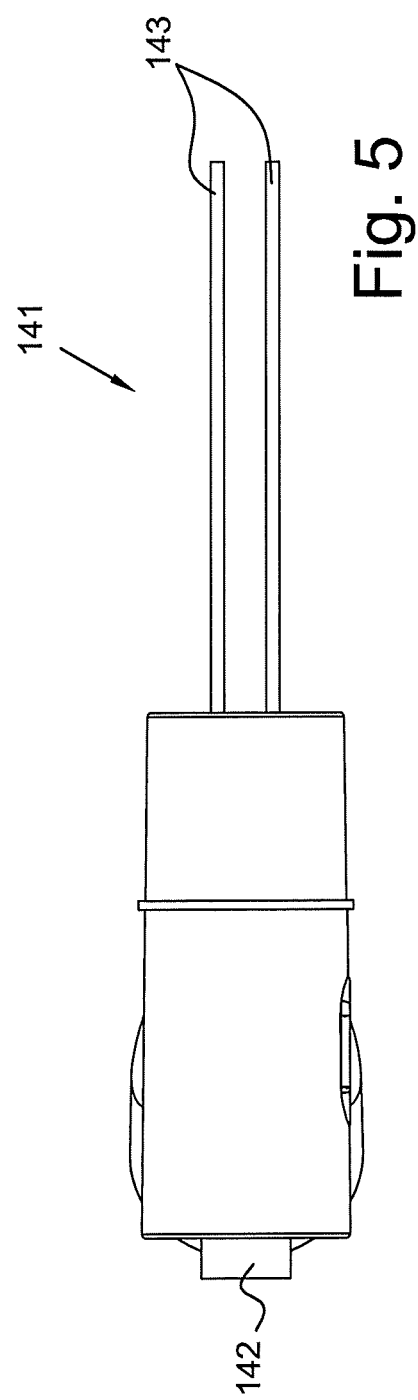

METHOD FOR CONTROLLING A THERMOREGULATED VENTILATION CIRCUIT

The present invention relates to a method for controlling a thermoregulated ventilation circuit comprising an active humidifier and a circuit integrating such active humidifier for actuating such method.

It is known that in normal respiration in a healthy subject the upper airways contribute to heating and humidifying the air inhaled and retaining the heat and humidity contained in the air exhaled, in order to release them during the next breath.

During natural inhalation, ambient air is normally heated until it reaches 37° C., at the branching level, between the trachea and the bronchi, the so-called "Carina" and completely 100% saturated up to contain 44 mg of water per litre of ventilated air.

On the contrary, in invasive mechanical ventilation, the patient's upper airways are bypassed by the introduction of the tracheal tube. Consequently, inspired gases reach the patient's lungs, which are colder and drier with respect to what happens in normal respiration without a by-pass. Thus, the normal exchange process (absorption and transfer of heat and humidity by the airways during respiration) is absent.

Prolonged exposure of the delicate lung tissues and the mucociliary epithelium to the improperly conditioned ventilation gases can determine numerous problems, including, for example localized inflammation of the trachea, the reduction in ciliary function, retention and thickening of secretions, lowering of the patient's body temperature, the reduction in cardiopulmonary function, increased risks of occlusion of the tracheal tube.

These drawbacks are overcome by humidifying and heating in advance the gases inspired by the patient.

The existing heating systems traditionally used for conditioning the inspired gases, called active humidifiers, are made up of an electrical device, comprising electrical power systems and the electronic systems for controlling the temperatures and a user interface, and of a disposable system for conveying and conditioning the respiratory gases made up of a circuit of tubes and a chamber for containing the water to be heated, which is usually disposable, the so-called cartridge.

Electrical resistance permanently contained in the body of the active humidifier heats a metal conduction element of the temperature, usually made of steel, which is placed in contact with the metal surface of the disposable cartridge, resting thereon. The water contained in the disposable cartridge is thus heated through the metal surface with which it is in direct contact.

The water heats and humidifies the residual volume of air contained in the cartridge so that the inspiratory gases crossing the cartridge, which can be both alternating and constant, are conveyed by the circuit, heated and humidified taking the residual volume of gas already present in the same cartridge and sent to the patient.

A series of temperature sensors placed at the exit of the disposable cartridge and at the end of the inspiratory tube, control the temperature value of the inspiratory gases and, consequently, regulate the energy value, which the electrical resistance immersed in the heating element supplies to the surface of the disposable cartridge to heat the water contained therein, which, in turn, transfers heat and humidity to the gases, which cross it, trying to keep the temperature value of the aforesaid gases at the value pre-set on the active humidifier by the health worker.

According to the methods for controlling the humidifier of the known type, the health worker sets the desired temperature of the inspiratory gases on the active humidifier and the heating means heat the metal element with which such heating means are in contact.

The metal element of the active humidifier transfers thermal energy by conduction to the metal surface of the cartridge, and the surface of the cartridge transfers thermal energy, in turn, again by conduction, to the water contained in the cartridge.

The hot water contained in the disposable cartridge transfers temperature and humidity to the residual volume of gas present in the same cartridge; the tubes, which convey the respiratory gases, take the cold, dry air from a source placed upstream of the cartridge inside the same cartridge; the water heated in the cartridge transfers temperature and humidity to the inspiratory gases, which cross it; on crossing the heated disposable cartridge, the inspiratory gases are thus charged with heat (and consequently increase in temperature) and humidity, and are conditioned at the value pre-set on the active humidifier.

On exiting the heating cartridge, the inspiratory gases are conveyed to the patient.

The temperature sensors placed at the exit of the heating cartridge, close to the patient's airway, control the temperature values of the gases conveyed to the patient in order to reach and maintain the value set on the active humidifier.

It follows that active humidifiers of the known type supply conditioned gases exiting at a temperature and humidity value preselected by the health worker. Said exiting gases are thus conveyed at the constant temperature and humidity values pre-set by the health workers, regardless of the conditions of the patient's body temperature.

However, the patient's body temperature can vary several times throughout one same day, and a different quantity of heat and humidity exhaled by the patient and conveyed to the expired gases corresponds to a change in the patient's body temperature. Consequently, a change in the patient's body temperature corresponds to a change in the quantity of heat and humidity exhaled, and thus lost, by the patient.

Insufficient humidification and heating can cause tracheal inflammations and ulcerations of the tracheo-bronchial mucosa, loss of body heat and water, retention of secretions, which become dense and viscous, thus reducing the efficacy of ciliary activity. This can lead to increased respiratory effort, to reductions in the lumen or obstructions of the tracheal tube placed in the airways and to frequent bronchopulmonary infections and atelectasis.

Whereas, excess humidification can reduce the viscosity of the secretions, increase mucociliary clearance, dilute the alveolar surfactant and cause leukocyte (neutrophil) infiltrations of bronchioles and lungs. All this gives rise to retention of secretions, atelectasis, worsening of pulmonary compliance, an increase in the gradient of alveolar and arterial oxygen.

All changes, which, if exacerbated, can result in consequences, such as pulmonary oedema or a generalised weight increase, hyponatremia and increased local susceptibility to bacterial infections, with a risk of broncho-pneumonia.

Whereas, excessive heat in the respiratory tree can cause desquamation of the mucosa, weakening of clearance, fibrin deposits in the small airways; all situations capable of creating mechanical obstructions, with everything that this involves.

However, as said, the inspiratory gases exiting the humidifier are at a constant fixed temperature and humidity value, a value predetermined by the health worker and decided as a function of the patient's body temperature in that particular moment and which corresponds to the best value decided by the worker in that given moment. As known and previously described, patient's body temperature can change several times throughout the same day, and a change in the patient's body temperature corresponds to a different quantity of heat and humidity exhaled by the patient and conveyed to the exhaled gases. Consequently, a change in the patient's body temperature corresponds to a change in the quantity of heat and humidity exhaled by the patient. The ideal situation would be for health workers to check these changes in the patient's body temperature several times and, consequently, adapt the temperature setting of the active humidifier. Clearly, this "ideal" procedure cannot be applied in the clinical reality for various reasons, such as a shortage of staff and a chronic lack of time to best perform all the various functions. It follows that the thermal adjustment of the active humidifier is carried out, in maximum operating conditions, two, or at most, three times in the space of 24 hours, usually during the inspection round and at the health worker shift changes.

Such condition does not allow optimum performance of the humidifier as exiting conditioned gases are not supplied at optimal temperature and humidity values for the patient, since they are closer to physiological values.

If the temperature and humidity values of the gases supplied to the patient are not optimal from a physiological point of view, the efficiency of the humidification process is compromised.

As said, only the attention, sensitivity and experience of the health worker allows the temperature value pre-set on the active humidifier to be changed coherently when there is a change in the patient's body temperature, an operation, which should be carried out several times throughout the same day but, which, as described, isn't.

Thus, it is a task of the present invention to provide a method for controlling a thermoregulated ventilation circuit comprising an active humidifier, which allows optimum efficiency of the humidifier to be obtained, enabling the temperature and humidity values of the gas supplied by the humidifier to be adapted automatically to the value of the patient's body temperature.

In such task, it is an object of the present invention to provide a method for controlling a thermoregulated ventilation circuit comprising an active humidifier, which makes it possible to adapt and have, at all times, the temperature and humidity values of the gases exiting the humidifier, manually or automatically.

This task and these other objects according to the present invention are achieved by providing a method for controlling a thermoregulated ventilation circuit comprising an active humidifier according to what is described in claim 1.

Further features of the method for controlling a thermoregulated ventilation circuit comprising an active humidifier and of the circuit suitable for actuating such control method are provided in the dependent claims.

The steps and advantages of the method for controlling a thermoregulated ventilation circuit comprising an active humidifier according to the present invention will be more apparent from the following description, which is given by way of a non-limiting example, with reference to the appended schematic drawings, wherein:

FIG. 1 schematically shows a thermoregulated circuit comprising an active humidifier suitable for actuating the method according to the invention;

FIGS. 2 and 3 are a side view and a plan view respectively of a first connection of the circuit in FIG. 1 for the intake tube, integrating an electrical connector for an electrical resistance, for two thermistors and for the connector for the connection of a patient's temperature probe;

FIGS. 4 and 5 are a side view and a plan view respectively of a second connector of the circuit in FIG. 1 for the exhalation tube comprising an electrical connector for an electrical resistance.

Figure 1:
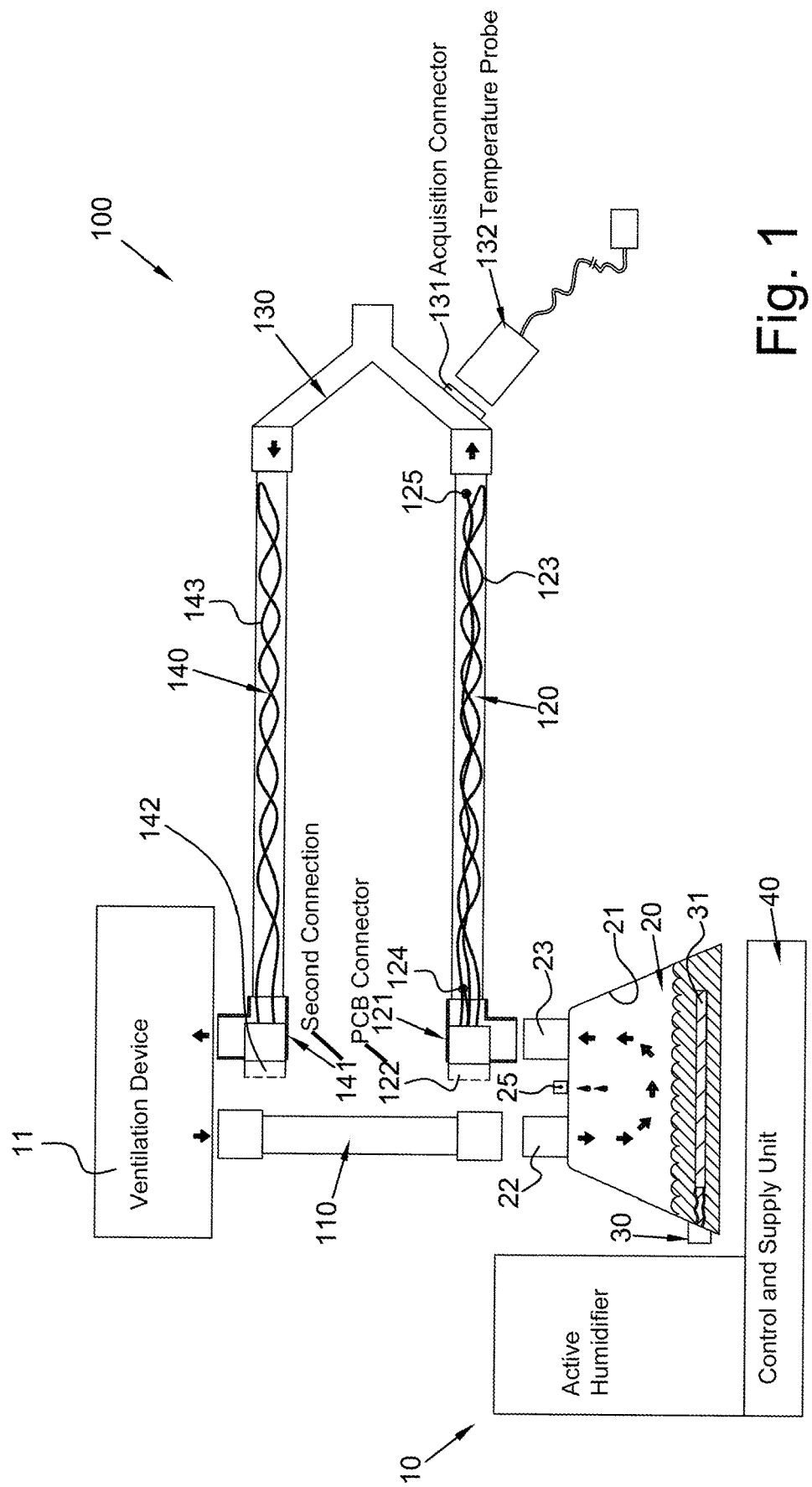

With reference to the figures, and in particular with reference to FIG. 1, a thermoregulated circuit 100 is shown comprising an active humidifier, globally indicated with numeral reference 10.

An active humidifier 10 comprises, in turn, a cartridge 20, preferably disposable, comprising a humidification chamber 21 adapted for containing water to be heated for the humidification of the air, an inlet opening 22 for air introduced by a ventilation device 11 and an outlet opening 23 for conditioned air exiting the humidifier.

The cartridge 20 comprises a heating element 30 comprising an electric resistance 31 for the heating of the water contained in the humidification chamber 21.

According to a preferred embodiment of the thermoregulated circuit 100 according to the present invention the water contained in the cartridge 20 and in direct contact with the heating element 30 is quickly heated.

The residual volume of the cartridge 20, not occupied by the liquid, is quickly heated, in turn, by the water contained in the cartridge 20, so that the gases from the ventilation device 11, which cross the residual volume of the cartridge 20, are quickly heated and humidified before being conveyed towards the outlet opening 23.

The thermoregulated circuit 100 according to the present invention comprises a unit for controlling and supplying 40 the cartridge 20, preferably provided with a user interface panel (not shown in the figures), for displaying and setting the operating parameters of the active humidifier 10.

According to the preferred embodiment of the present invention, the thermoregulated circuit 100 for patient ventilation comprises the active humidifier indicated with numeral reference 10 and, by means of the control unit 40, it is also possible to set the temperature of the heating means 123 of the air exiting the cartridge 20, advantageously formed by an electrical resistance 123, preferably a wire heating element, placed inside the intake tube 120 inside which the air exiting the cartridge 20 is conveyed. Advantageously, the thermoregulated circuit 100 comprises a first tube 110 for introducing air from the ventilation device 11, connected to the air inlet opening 22 of cartridge 20. The air passing through this tube, which is not conditioned, generally has a room temperature between 18-23° C.

The thermoregulated circuit 100 also comprises an intake tube 120 connected at a first end thereof to the outlet opening 23 for conditioned air of the cartridge 20 by means of a first connection 121 and at an opposite end thereof connected to a Y connection 130 for respiratory interfacing with the patient.

Advantageously, the intake tube 120 is provided with a wire heating element 123 arranged along the entire longitudinal development thereof, as well as with a first thermistor 124, placed close to the outlet of the cartridge 20, and with a second thermistor 125, placed close to the connection with the patient, placed at opposite ends respectively of the intake tube 120.

The management of the power supplied to the wire heating element 123 is controlled by the second thermistor 125 placed close to the connection with the patient.

Preferably, the thermoregulated circuit 100 further comprises an exhalation tube 140, connected at a first end to the Y connection 130 for respiratory interfacing and it is provided with a wire heating element 143 arranged along the entire longitudinal development thereof. The opposite end of the exhalation tube 140 is connected to the ventilation device 11.

The air from the exhalation tube 140 exhaled by the patient, which returns to the ventilation device 11 through the Y connection 130, has a temperature of about 34° C., while, on exiting the exhalation tube 140 it will have been heated to keep an equal or greater temperature value.

According to a preferred aspect of the invention the Y connection 130 for respiratory interfacing comprises an acquisition connector 131 for the connection of a patient's temperature probe 132 of the known standardised type, shown schematically in FIG. 1.

The temperature probe 132 is of a type known for some time on the market and used daily in critical hospital wards for the continuous detection of the patient's body temperature. Such probes can be positioned in the oesophagus, in the pulmonary artery, in the bladder or in the eardrum and they are fitted with a standardised connector.

The method for controlling the active humidifier 10 according to the present invention is based on the acquisition by the active humidifier 10 of the value of the patient's body temperature Tp through the direct connection with a patient's temperature probe 132.

Advantageously, both the measuring by the temperature probe 132 and the acquisition of such temperature value Tp by the control unit 40 are carried out continuously.

More specifically, the method for controlling the thermoregulated ventilation circuit 100 equipped with a control unit 40 and comprising an active humidifier 10 according to the present invention allows the operation of the humidifier to be controlled automatically, adjusting the same automatically to changes in the patient's temperature read by the temperature probe 132 and consequently regulating the thermoregulated circuit 100, in particular, supplying optimum inspiratory gases proportionate to the aforesaid changes in temperature, improving the patient's respiratory comfort.

Advantageously, the control unit 40 receives in input the patient's temperature data Tp detected by the patient's temperature probe 132 and regulates the operation of said heating element 30 of the cartridge 20 and the operation of the heating means 123 of the air exiting said cartridge 20 as a function of the patient's temperature Tp.

Advantageously, the patient's temperature Tp is detected continuously by said patient's temperature probe 132 and the control unit 40 continuously receives the patient's temperature data Tp in input and regulates the operation of the heating element 30 and the operation of the heating means 123 of the air upon any change of the patient's temperature Tp.

The control unit 40 acts on the heating means 123 of the air so that the temperature of the air exiting the ventilation circuit 100 is substantially conform and appropriate for the patient's temperature Tp detected by said patient's temperature probe 132.

The acquisition of the data Tp allows the temperature of the inspiratory gases to be regulated automatically when there is a change in patient's body temperature, thus improving respiratory comfort and maintaining a better and more suitable fluidification of the bronchial secretions.

Advantageously, the control unit 40 receives in input, as well as the patient's temperature Tp, the value of the temperature of the air exiting the cartridge 20 read by a first thermistor 124, and advantageously, also the value of the temperature of the air exiting the intake tube 120 detected by a second thermistor 125.

Advantageously, the control unit 40 regulates the electric power supplied to said heating element 30 of the cartridge 20 based on the temperature value read by the first thermistor 124, and the electric power supplied to said heating means 123 for heating the air exiting said cartridge 20 based on the temperature value read by the second thermistor 125.

Advantageously, the control unit 40 is equipped with a control display so that the user can set the adjustment of the circuit parameters manually, always benefiting from the data relating to patient's temperature Tp when manually adjusting the temperature parameters of the air exiting the intake tube 120 and the humidity value contained in such air.

Preferably, the method for controlling a thermoregulated ventilation circuit 100 according to the present invention provides for the control unit 40 receiving in input the value of the inner temperature of the heating element 30 of said cartridge 20 from a thermistor integrated in said heating element 30.

Going back to the description of the ventilation circuit 100, according to the invention, in the first connection 121 converge a pair of electrical resistance wires 123, a pair of wires for each of the two thermistors 124 and 125 and a pair of wires, not shown in FIG. 1, of the acquisition connector 131 of the patient's temperature probe 132.

A printed circuit board connector (PCB) 122, integrated in the first connection 121 of the intake tube 120, realizes the electric power supply of the resistance 123, the acquisition of the thermistors 124, 125 and the acquisition of the patient's temperature probe associated with the intake tube 120.

In particular, the first thermistor 124 is placed in the centre of the inspiratory gas flow, in the exit connection 121 of the gases from the cartridge 20.

The welding of the first thermistor 124 and the pair of wires thereof on the PCB connector 122 guarantees the same positioning of the temperature sensor on each single thermoregulated circuit 100 produced.

The reading made by such first thermistor 124 guarantees the perfect regulation of the power supplied and to be supplied to the electrical resistance 31 positioned inside the humidification chamber 21, so as to keep the temperature value of the water constant, when the gas flow crossing it varies, and, consequently, the temperature value of the gases supplied to the patient.

The function of the second thermistor 125 placed close to the patient connection is to control and adjust the power supplied to the resistance 123 placed inside the intake tube 120. Such resistance 123 has the task of keeping the temperature of the air exiting the cartridge 20 constant and thus avoiding the formation of condensation inside the intake tube 120, which is caused by the drop in temperature during the way from the cartridge 20 to the patient.

The exhalation tube 140 is connected at the opposite end to a second connection 141, which can be connected to the ventilation device 11.

Advantageously, a pair of electrical resistance wires 143 converge in the second connection 141, which are supplied electrically by means of a printed circuit board connector (PCB) 142, integrated in the second connection 141 of the exhalation tube 140.

The function of the electrical resistance 143 placed inside the exhalation tube 140 is to avoid the formation of condensation also inside this part of the circuit. Considering that the temperature of the gases exhaled by the patient is practically constant, about 34° C., it is possible to avoid controlling the power of such resistance 143, also considering that the heating of the air inside the exhalation tube 140 at greater values than those inhaled poses no problem, being the same downstream of the patient.

It was thus shown how the method for controlling a thermoregulated ventilation circuit according to the present invention obtains the stated advantages. More specifically, among the advantages of the method according to the present invention is that of being able to implement an automatic feedback based on the patient's body temperature acquired by the system.

In fact, it was pointed out how patient's body temperature can vary several times throughout the same day. A different temperature and humidity quantity transferred in the gases exhaled by the same patient corresponds to a change in patient's body temperature.

Being able to condition the inspiratory gases dependently of the patient's body temperature value and the changes thereof instantly offers practical advantages for health workers and comfort for the patient.

A method for controlling a thermoregulated ventilation circuit comprising an active humidifier and a thermoregulated circuit integrating such active humidifier thus conceived are susceptible to numerous modifications and variations, all falling within the invention.

Furthermore, all of the details can be replaced by technically equivalent elements.

The invention claimed is:

1. A method for controlling a thermoregulated ventilation circuit equipped with a control unit and comprising an active humidifier, said active humidifier comprising, in turn, a cartridge provided with a humidification chamber adapted to contain water to be heated for the humidification of the air through a heating element, said thermoregulated circuit also comprising at least one intake tube for conveying the air exiting said cartridge and equipped with heating means for heating the air exiting said cartridge, the method comprising:

said control unit receiving an input of a patient's body temperature data detected by a patient's internal body temperature probe; and automatically regulating the operation of said heating element of said cartridge and the operation of said heating means of the air exiting said cartridge as a function of said patient's body temperature.

2. The method for controlling a thermoregulated ventilation circuit according to claim 1, wherein said patient's body temperature is detected continuously by said patient's internal body temperature probe, and said control unit continuously receives the patient's body temperature data in input and regulates the operation of said heating element and said heating means of the air with every change in patient's body temperature.

3. The method for controlling a thermoregulated ventilation circuit according to claim 2, wherein said control unit acts on the heating means of the air so that the temperature of the air exiting the ventilation circuit is automatically regulated by the control unit based on the patient's body temperature detected by said patient's internal body temperature probe.

4. The method for controlling a thermoregulated ventilation circuit according to claim 3, wherein said control unit receives in input, as well as the patient's body temperature, the value of the temperature of the air exiting the cartridge read by a first thermistor.

5. The method for controlling a thermoregulated ventilation circuit according to claim 4, wherein said control unit also receives as input data the temperature value of the air exiting the intake tube detected by a second thermistor.

6. The method for controlling a thermoregulated ventilation circuit according to claim 5, wherein said control unit regulates the electric power supplied to said heating element of said cartridge based on the temperature value read by said first thermistor.

7. The method for controlling a thermoregulated ventilation circuit according to claim 5, wherein said control unit regulates the electric power supplied to said heating means for heating the air exiting said cartridge based on the temperature value read by said second thermistor.

8. The method for controlling a thermoregulated ventilation circuit according to claim 1, wherein said control unit is equipped with a control display so as to allow the manual adjustment of the temperature parameters of the air exiting the intake tube and of the value of humidity contained in such air to be set by the user.

9. The method for controlling a thermoregulated ventilation circuit according to claim 1, wherein said control unit receives in input the value of the inner temperature of the heating element of said cartridge from a thermistor integrated in said heating element.

10. A thermoregulated ventilation circuit comprising:

an active humidifier, comprising, in turn, at least one cartridge provided with a humidification chamber adapted for containing water to be heated for the humidification of the air through a heating element;

at least one intake tube to convey the air exiting said cartridge and equipped with heating means for heating the air exiting said cartridge;

at least one acquisition connector for the connection of a patient's temperature probe; and a control unit configured to receive in input patient's body temperature data detected by said patient's internal body temperature probe, and regulate the operation of said heating element of said cartridge and the operation of said heating means of the air exiting said cartridge as a function of said patient's body temperature.

* * * * *